US00PP17419P2

(12) United States Plant Patent
Larsen

(10) Patent No.: US PP17,419 P2
(45) Date of Patent: Feb. 20, 2007

(54) ***OSTEOSPERMUM* PLANT NAMED 'SUNNY FELIX'**

(50) Latin Name: *Osteospermum ecklonis (DC) T. Norl.*
Varietal Denomination: Sunny Felix

(75) Inventor: Bjarne Nyholm Larsen, Odense N (DK)

(73) Assignee: Sunny Osteospermum APS, Odense N (DK)

( * ) Notice: Subject to any disclaimer, the term of this patent is extended or adjusted under 35 U.S.C. 154(b) by 14 days.

(21) Appl. No.: 11/234,146

(22) Filed: Sep. 26, 2005

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent Bell
(74) *Attorney, Agent, or Firm*—Foley & Lardner LLP

(57) ABSTRACT

A new distinct cultivar of *Osteospermum* plant named 'Sunny Felix', characterized by its white ray florets with a small, but distinct violet-blue spot, violet-blue to gray-purple disc florets, dark green foliage, long ray florets measuring about 37 mm in length, and more leaves and shorter petioles than the typical *Osteospermum* variety.

3 Drawing Sheets

Botanical designation: *Osteospermum ecklonis* (*DC*) *T. Norl.*
Variety denomination: 'Sunny Felix'.

BACKGROUND OF THE INVENTION

The present Invention relates to a new and distinct cultivar of *Osteospermum* plant, botanically known as *Osteospermum ecklonis* (*DC*) *T. Norl.*, commonly known as Cape Daisy, and hereinafter referred to by the variety denomination 'Sunny Felix'.

The new *Osteospermum* is a product of a planned breeding program conducted by the inventor, Bjarne Larsen, in Stige, Odense, Denmark. The objective of the breeding program is to develop a new *Osteospermum* variety with inverted conical, compact, and upright plant habit, interesting inflorescence color, and good keeping quality.

The new *Osteospermum* originated from a planned crossing of two selected parent plants made by the inventor in 2002 in Stige, Odense, Denmark. The female or seed parent is an *Osteospermum ecklonis* (*DC*) *T. Norl.* cultivar designated '2.298.98' (unpatented). The male or pollen parent is an *Osteospermum ecklonis* (*DC*) *T. Norl.* cultivar designated '9913' (unpatented). The new *Osteospermum* cultivar 'Sunny Felix' was selected by the inventor as a single flowering plant within the progeny of the above crossing in 2003 in a controlled environment in Stige, Odense, Denmark.

Asexual reproduction of the new *Osteospermum* cultivar by apical stem cutting was first performed in February of 2003 in Stige, Odense, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'Sunny Felix'. These characteristics in combination distinguish 'Sunny Felix' as a new and distinct cultivar:

1. White ray florets with a small, but distinct violet-blue spot;
2. Violet-blue to gray-purple disc florets;
3. Dark green foliage;
4. Long ray florets, measuring about 37 mm in length; and
5. More leaves and shorter petioles than a typical *Osteospermum* variety.

Plants of the parental cultivars, '2.298.98' (unpatented) and '9913' (unpatented) are not longer unavailable to provide a botanical comparison to plants of the new cultivar 'Sunny Felix'.

Of the many commercial cultivars known to the present inventor, the most similar in comparison to the new *Osteospermum* cultivar 'Sunny Felix' is the *Osteospermum* cultivar 'Sunny Cecil', (patented, U.S. Plant Pat. No. 15,273). In side-by-side comparisons conducted in Stige, Denmark, plants of 'Sunny Felix' differed from plants of 'Sunny Cecil' in the characteristics described in Table 1:

TABLE 1

| Trait | New Cultivar 'Sunny Felix' | Female Parent 'Sunny Cecil' (patented) |
|---|---|---|
| Overall Plant Shape | Inverted conical, upright | Globular, upright |
| Number of Lateral Branches | 4 primary, 9 secondary (flowering) | 4 primary, 17 secondary |
| Lateral Branch Length | Primary: 5 cm, Secondary: 8–14 cm (incl. inflorescence) | Primary: About 3 cm, Secondary: 7–12 cm |
| Quantity of Leaves per Lateral Branch | 25–31 | 10–15 |
| Internode Length | 17 mm | About 3 mm |
| Foliage Color | Young, upper side: RHS 139A<br>Young, underside: RHS 137C<br>Mature, upper side: RHS 137B<br>Mature, under side: RHS 138A | Young, upper side: RHS 147A<br>Young, underside: RHS 139B<br>Mature, upper side: RHS 147A<br>Mature, under side: RHS 147A |
| Petiole Length: | 5–10 mm | 10–30 mm |

TABLE 1-continued

| Trait | New Cultivar 'Sunny Felix' | Female Parent 'Sunny Cecil' (patented) |
|---|---|---|
| Ray Floret Color (upper side, fully opened) | White, RHS N155C, with a small violet-blue spot, RHS 92A, at apex | White, RHS 155D |
| Disc Floret Color (upper side, when opening) | Violet-blue, RHS N92A | Gray-purple, RHS 186A |
| Peduncle Length | 9–12 cm | 7–10 cm |
| Anther Color | Black (Grey Group), RHS 202A | Blue RHS N99B |

BRIEF DESCRIPTION OF THE PHOTOGRAPHS

The accompanying colored photographs illustrate the overall appearance of the new *Osteospermum* cultivar 'Sunny Felix' showing the colors as true as is reasonably possible with colored reproductions of this type. Colors in the photographs may differ slightly from the color values cited in the detailed botanical description which accurately describe the color of the new *Osteospermum* cultivar 'Sunny Felix'.

DETAILED BOTANICAL DESCRIPTION

Figure 1:
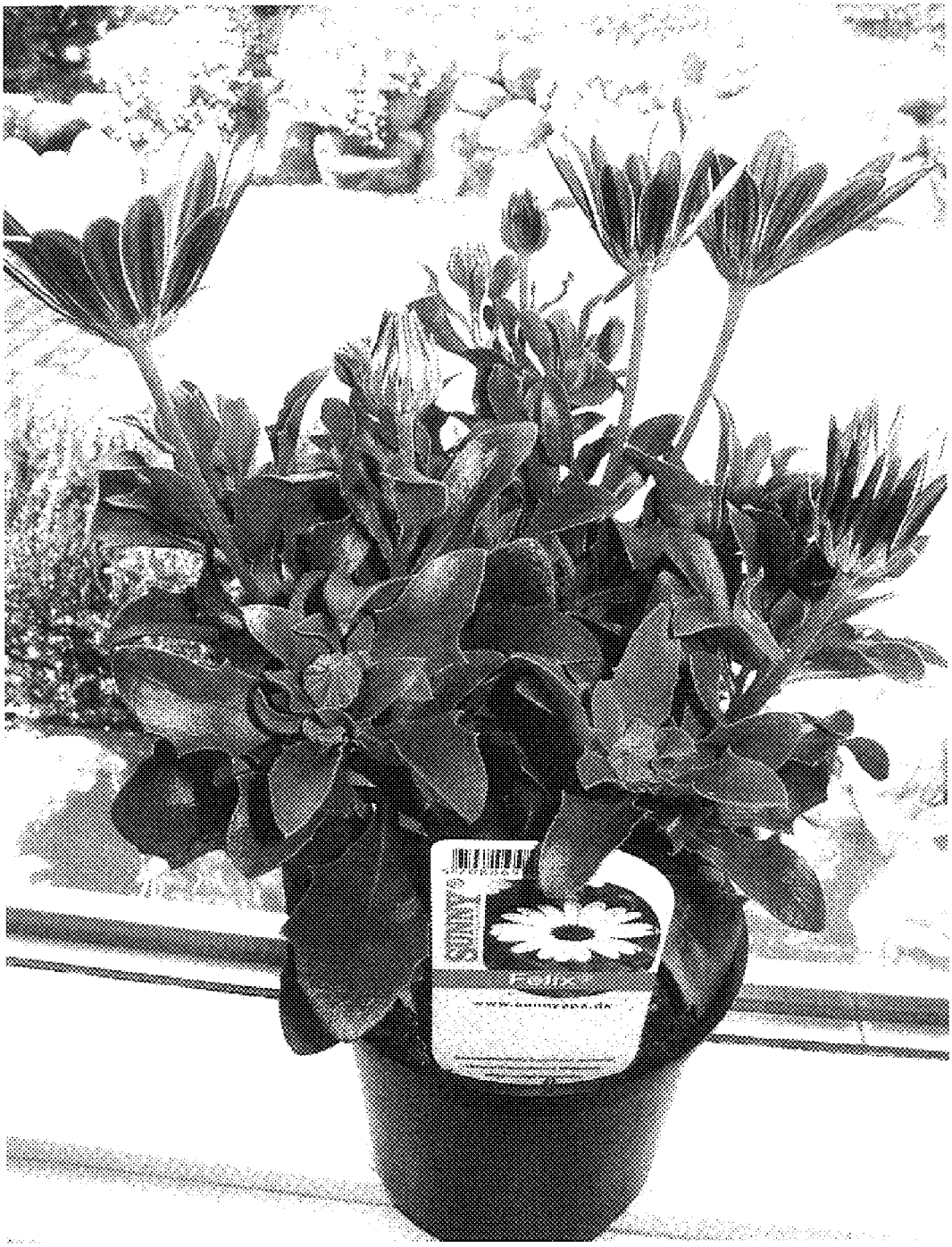
FIG. 1 shows a side perspective view of a typical potted flowering plant of 'Sunny Felix', as a produced cultivar, 20 weeks after planting.
Figure 2:
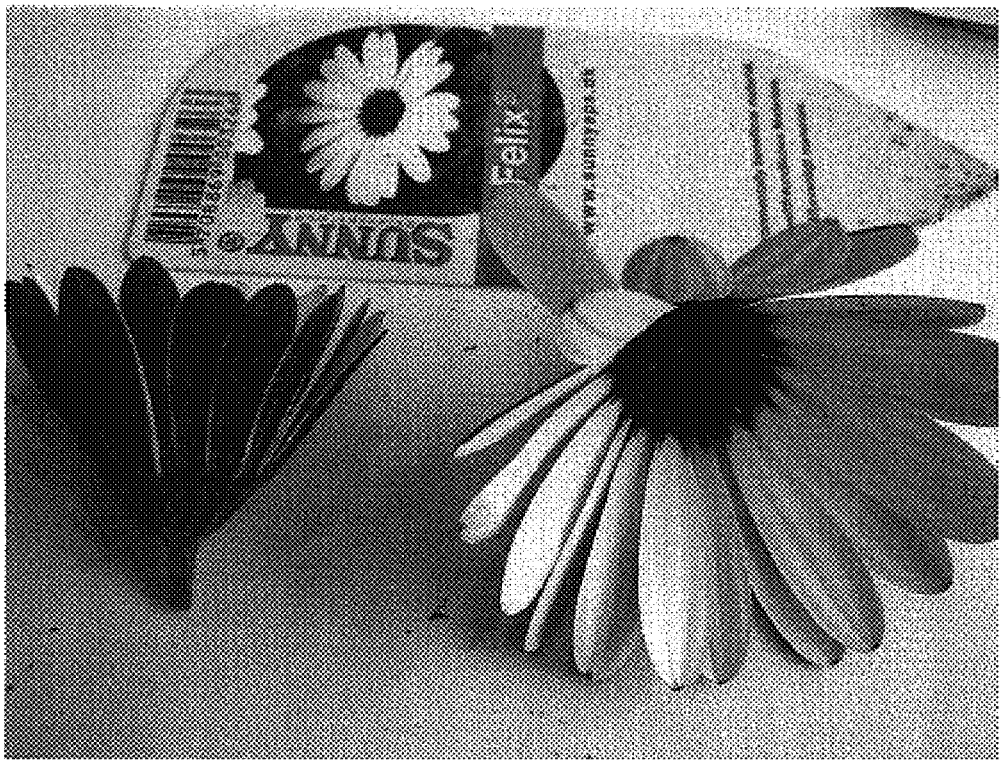
FIG. 2 shows a top and bottom perspective view of inflorescences of 'Sunny Felix', as a produced cultivar, 20 weeks after planting.
Figure 3:
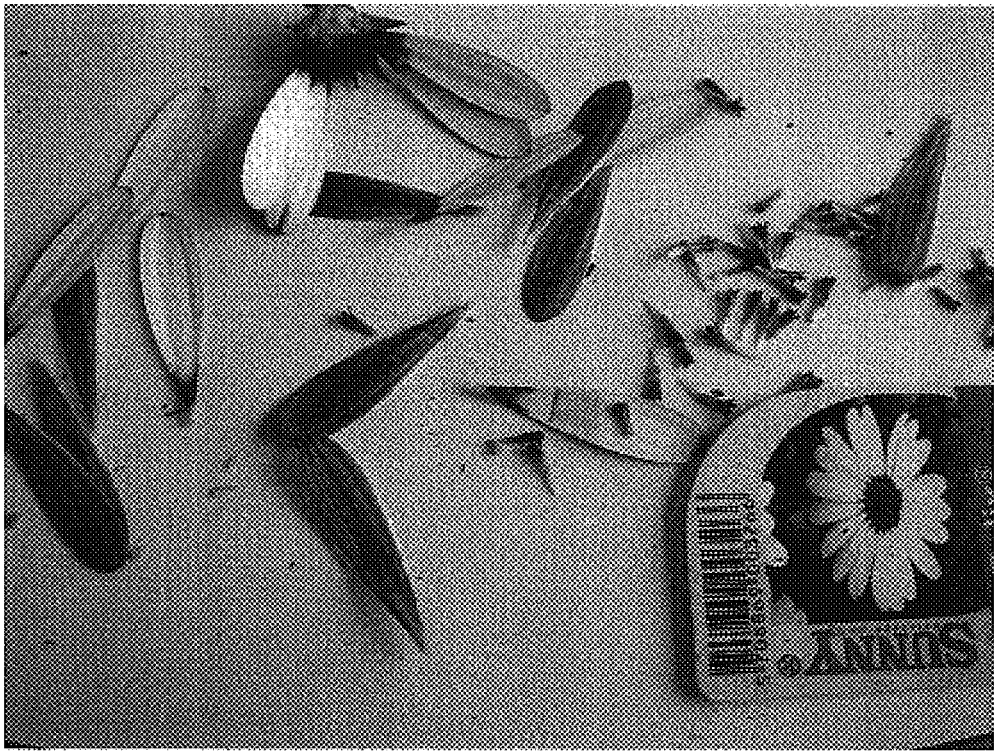
FIG. 3 shows a dissected view of a typical flower of 'Sunny Felix', as a produced cultivar, 20 weeks after planting.
Figure 4:
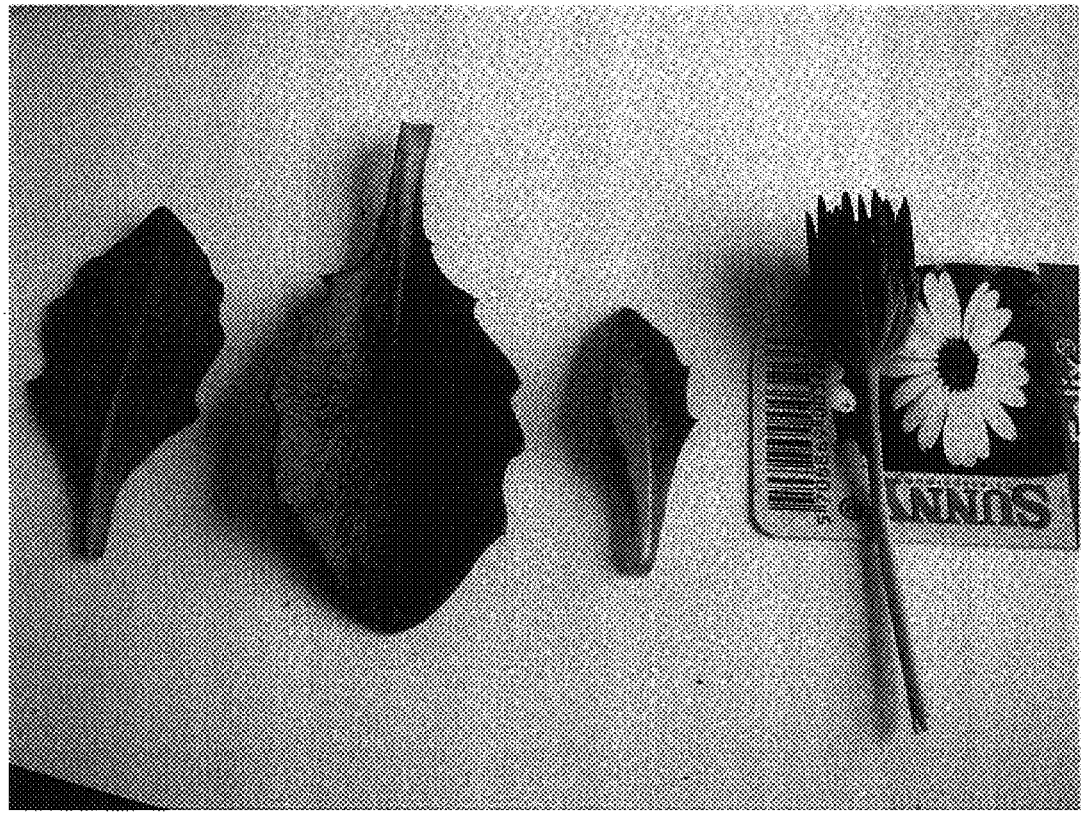
FIG. 4 shows a view of typical leaves and bud of 'Sunny Felix', as a produced cultivar, 20 weeks after planting.

The new *Osteospermum* cultivar 'Sunny Felix' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new *Osteospermum* cultivar 'Sunny Felix' as grown in a greenhouse in Stige, Odense, Denmark, under conditions which closely approximate those generally used in commercial practice and garden use Vegetative propagation with apical tip cuttings (4–5 leaves) took place in a greenhouse with propagation tents for 3 weeks with the day and night temperature averaging about 20° C. The temperature was then lowered to the day and night temperature averaging about 14° C. The plants were subirrigated with a nutrient solution of 2–3 mS when needed and given supplementary irradiation with SON T lamps having an installed energy level of 400 $Wm^2$.

Color references are made to The Royal Horticultural Society Colour Chart (R.H.S.), $4^{th}$ edition 2000, except where general colors of ordinary significance are used. The photographs and descriptions were taken during the spring season when outdoor day temperatures ranged from 7° C. to 15° C. and outdoor night temperatures ranged from 0° C. to 7° C. The age of the plants described is 20 weeks.

Botanical classification: *Osteospermum ecklonis* (*DC*) *T. Norl.*

Parentage:

*Female or seed parent.*—*Osteospermum ecklonis* (*DC*) *T. Norl.* designated '2.298.98' (unpatented).

*Male or pollen parent.*—*Osteospermum ecklonis* (*DC*) *T. Norl.* designated '9913' (unpatented).

Propagation:

*Type.*—Apical stem cutting.

*Time and temperature to initiate roots.*—Summer: About 12 to 14 days at 20° C. to 22° C. in tunnels in a greenhouse. Winter: About 17 to 20 days at 20° C. to 22° C. in tunnels in a greenhouse.

*Time and temperature to develop roots.*—Summer: About 14 to 18 days at 20° C. to 22° C. in tunnels in a greenhouse. Winter: About 20 to 22 days at 20° C. to 22° C. in tunnels in a greenhouse.

*Rooting description.*—100% rooting.

*Rooting habit.*—Fine, fibrous and branching.

*Root color.*—White, RHS 155D.

*Root texture.*—Coarse.

Plant description:

*General appearance and form.*—Perennial plant with upright plant habit used as a bedding or potted plant. *Osteospermum* inflorescences in composite heads, daisy type.

*Growth and branching habit.*—Freely branching with lateral flowering branches forming at every node; dense and bushy.

*Growth rate/vigor.*—Vigorous.

*Plant height* (*soil level to top of plant plane*).—About 20 cm, Range: 18–22.

*Plant width* (*spread*).—About 17 cm, Range: 15–19.

*Plant strength.*—Low temperature tolerance: Withstands temperatures down to +1° C. High temperature tolerance: Not tested over +30° C., but flowering ceases over 28° C.

*Crop time to produce a mature flowering plant.*—After rooting, about 16 weeks are required to produce finished flowering plants in 11 cm pots.

Branches:

*Number of branches per plant.*—4 primary, 9 secondary.

*Length.*—Primary: About 5 cm. Secondary: 8–14 cm (including inflorescence).

*Diameter.*—About 4–5 mm.

*Internode length.*—Average 17 mm, Range 9–29 mm.

*Strength.*—Sturdy.

*Aspect.*—Upright, branches at 70° angle.

*Texture.*—Glabrous.

*Color.*—Yellow-green, RHS 144C.

Foliage description:

*Arrangement.*—Alternate (5-whorl), single, lobed, obovate to lanceolate.

*Length.*—About 3–7 cm.

*Width.*—About 1–3 cm.

*Overall shape of leaf.*—Obovate to lanceolate, lobed.

*Shape at apex.*—Mature leaf: obtuse. Young leaf: subacute.

*Shape at base.*—Attenuate, decurrent.

*Margin.*—Lobed, pinnateilobate (4–6 acute lobes).

*Texture.*—Scattered, short stiff hairs along veins and edges.

*Color of developing foliage.*—Upper surface: RHS 139A, green. Lower surface: RHS 137C, green.

*Color of mature foliage.*—Upper surface: 137B, green. Lower surface: 138A, green.
*Venation pattern.*—Brochidodromus, form of pinnate.
*Venation color.*—Upper surface: Not visible against background tissue. Lower surface: RHS 138B, green.
*Petiole length.*—About 5–10 mm.
*Petiole diameter.*—About 2–4 mm (flat, winged).
*Petiole texture.*—Glabrous.
*Petiole color.*—Yellow-green, RHS 145B.

Inflorescence description:
*Appearance.*—Terminal and axillary inflorescences held above and beyond the foliage. Single, composite inflorescence form, radially symmetrical, with ligulate-shaped ray florets and disc florets massed at the center; ray and disc florets arranged acropetally on a capitulum. Inflorescences face upright with aspect of 80° C.
*Natural flowering season.*—Continuous throughout the spring and summer in temperature regions. Season can be extended by vernalization and long day treatments. Flowering may cease if temperatures exceed 28° C.
*Time to flower.*—5 to 10 days (longevity of individual inflorescences is dependent on temperature and light conditions).
*Postproduction longevity.*—Inflorescences maintain good color and substance for about 14 days on the plant when grown in an outdoor environment. Inflorescences persistent.
*Quantity of inflorescences.*—Freely flowering; more than 25 open inflorescences and inflorescence buds per plant.
*Rate of inflorescences opening.*—About 3 per week per plant, depending on light and temperature conditions.
*Fragrance.*—Flowers have a weak, fresh lemon scent.

Bud:
*Rate of opening (from showing color to fully open inflorescence).*—4 to 5 days.
*Length.*—About 0 to 16 mm at color showing.
*Diameter.*—About 0 to 10 mm.
*Shape.*—Globular until color, then ovoid.
*Color.*—From RHS 145C, yellow green (base) to yellow-green, RHS 146B (apex).

Peduncle:
*Length.*—Terminal: About 12 cm. Secondary: About 10 cm. Tertitiary: About 9 cm.
*Diameter.*—About 2–3 mm.
*Appearance and angle.*—Terminal: Erect. Secondary: About 10 to 25 degrees from vertical. Tertiary: About 30 to 80 degrees from vertical.
*Strength.*—Strong, stiff.
*Texture.*—Glabrous.
*Color.*—Yellow-green, RHS 144C.

Inflorescence:
*Inflorescence depth.*—About 2–3 cm.
*Inflorescence diameter.*—About 6–7 cm.
*Receptacle diameter.*—About 1.2 cm.
*Receptacle height.*—About 0.5 cm.
*Receptacle shape.*—Semi-globular.
*Receptacle color.*—Yellow-green, RHS 144D.

Ray florets:
*Quantity per inflorescence.*—Typical number: 20, overlapping. Observed number: 19–21.
*Length.*—About 37 mm. Range 35–39 mm.
*Width.*—About 8 mm.
*Overall shape.*—Elliptic, ligulate.
*Shape at apex.*—Acute with slight retuse tip.
*Shape at base.*—Attenuate.
*Margin.*—Entire.
*Texture.*—Upper surface: Shiny. Lower surface: Dull.
*Orientation.*—Initially 30 degrees from vertical, with development, close to 90 degrees from vertical.
*Color (upper surface).*—When opening & when fully opened: RHS N155C, white, with a small violet-blue spot at apex, RHS 92A.
*Color (lower surface).*—When opening: Base: RHS 92B, violet-blue, with stripes of RHS N79B, purple, alternating with RHS N80A, purple-violet When fully opened: Base: RHS 92B, violet-blue, with stripes now more RHS N80A, purple-violet.

Disc florets:
*Quantity per inflorescence.*—Typical number: 102. Observed number: 90–110.
*Length.*—About 10 mm.
*Width.*—At apex: About 4 mm. At base: About 1 mm.
*Disc area diameter.*—About 13 mm.
*Overall shape.*—Tubular.
*Shape at apex.*—Star.
*Shape at base.*—Fused.
*Margin.*—Entire.
*Texture.*—Upper surface: shiny, translucent. Lower surface: shiny, translucent.
*Color (when opening).*—Upper and lower surfaces: violet-blue, RHS N92A.
*Color (when fully opened).*—Upper and lower surfaces: gray-purple, RHS N187A.

Phyllaries:
*Quantity per inflorescence.*—About 20 units in a single whorl.
*Length.*—About 6 to 12 mm.
*Width.*—About 1–3 mm.
*Overall shape.*—Gladiate, basally fused.
*Shape at apex.*—Acute.
*Shape at base.*—Fused.
*Margin.*—Entire.
*Color.*—Upper side: green, RHS 137D (translucent edges). Under side: green, RHS 137C.

Reproductive organs:
Androecium: On disc florets only.
*Stamen number.*—5 per floret; fused around style.
*Stamen length.*—About 6 mm.
*Anther shape.*—Linear.
*Anther length.*—About 2 mm.
*Anther color.*—Black, RHS 202A.
*Pollen amount.*—Plenty.
*Pollen color.*—Orange, RHS N25A.

Gynoecium: On ray and disc florets only.
*Quantity.*—1 per floret.
*Pistil length.*—About 4 mm.
*Stigma shape.*—Brush-like.
*Stigma color.*—Purple, RHS N187A.
*Style length.*—About 2 mm.
*Style color.*—White, RHS N155D.
*Ovary color.*—Green-yellow, RHS 2D.

Seed: None observed at this stage of development.
Fruit: None observed.
Disease/pest resistance: Good.
Disease/pest susceptibility: No diseases observed.
Temperature tolerance: Plants of the new *Osteospermum* have exhibited good tolerance to draught, rain and wind, however flowering may cease during hot periods (temperatures above 28° C.). Low temperature tolerance to 1° C.

Growth retardant(s): 3 times 0.2% Chlormequat drench during production.

I claim:

1. A new and distinct cultivar of *Osteospermum* plant named 'Sunny Felix', as illustrated and described herein.

* * * * *